(12) United States Patent  (10) Patent No.: US 8,119,995 B2
Klunder et al.  (45) Date of Patent: Feb. 21, 2012

(54) DEVICE FOR DETECTION OF EXCITATION USING A MULTIPLE SPOT ARRANGEMENT

(75) Inventors: Derk Jan Wilfred Klunder, Geldrop (NL); Levinus Pieter Bakker, Helmond (NL); Sjoerd Stallinga, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 11/995,826

(22) PCT Filed: Jul. 17, 2006

(86) PCT No.: PCT/IB2006/052430
§ 371 (c)(1),
(2), (4) Date: Jan. 16, 2008

(87) PCT Pub. No.: WO2007/010469
PCT Pub. Date: Jan. 25, 2007

(65) Prior Publication Data
US 2008/0265175 A1 Oct. 30, 2008

(30) Foreign Application Priority Data
Jul. 21, 2005 (EP) .................................... 05106685
Nov. 23, 2005 (EP) .................................... 05111139

(51) Int. Cl.
*G01J 1/58* (2006.01)
(52) U.S. Cl. .................. 250/458.1; 250/459.1; 250/339; 356/419; 356/445; 356/244

(58) Field of Classification Search ............... 250/458.1, 250/339
See application file for complete search history.

(56) References Cited

U.S. PATENT DOCUMENTS

| 6,274,872 | B1 * | 8/2001 | Katerkamp | 250/458.1 |
| 6,300,638 | B1 * | 10/2001 | Groger et al. | 250/458.1 |
| 6,312,961 | B1 | 11/2001 | Voirin et al. | |
| 6,437,345 | B1 * | 8/2002 | Bruno-Raimondi et al. | 250/458.1 |
| 2001/0003043 | A1 | 6/2001 | Metspalu et al. | |
| 2004/0125370 | A1 * | 7/2004 | Montagu | 356/244 |

FOREIGN PATENT DOCUMENTS

| DE | 10017824 B4 | 3/2004 |
| EP | 1223421 A2 | 7/2002 |
| EP | 1384989 A1 | 1/2004 |
| WO | 0058715 A2 | 10/2000 |
| WO | WO0058715 * | 10/2000 |
| WO | 2006061783 A1 | 6/2006 |
| WO | 2006064465 A2 | 6/2006 |

OTHER PUBLICATIONS

Adolf W. Lohmann, et al: Making an Array Illuminator Based on the Talbot Effect, Applied Optics, OSA, Opt. Soc. of Am, vol. 29, No. 29, Oct. 10, 1990, pp. 4337-4340, XP002314360.

* cited by examiner

Primary Examiner — Sally Sakelaris

(57) ABSTRACT

The invention relates to a device (1) for detection of excitation (110) using a multiple spot arrangement (60), in which a multiple spot generator (50) is matched to the multiple spot arrangement (60) in such a way that light (100) entering the multiple spot generator (50) will be guided to defined areas on the multiple spot arrangement (60).

16 Claims, 3 Drawing Sheets

DEVICE FOR DETECTION OF EXCITATION USING A MULTIPLE SPOT ARRANGEMENT

The present invention is directed to the field of devices for detection of excitation, especially for evanescent field excitation.

In the field of devices for detection of excitation, especially for evanescent field excitation, which are used e.g. as biosensors, it has been common technique to use a prism, which has an interface with the sample (usually an aqueous medium or other fluid). Into the prism, a single spot or collimated beam of light of a certain wavelength is directed under an angle (with respect to the interface between the prism and the sample) larger than the total internal reflection angle. This results in an evanescent field at the interface with the sample. In case of absorption of the evanescent field by species present in the sample, this can result in the excitation of excited states, which can relax to the ground state by e.g., luminescence resulting in the generation of luminescent radiation. Usually the luminescence is caused by a luminescent, mostly fluorescent-labeled biomolecule such as a protein or a DNA or RNA-strand. The luminescence is then measured and the biomolecule identified.

However, directing a single spot or collimated beam into the prism bears the following problems:

In case of wide-field illumination; for this case a large area of the interface between the prism and the sample is illuminated by a single (e.g., collimated) beam. When only a few luminophores (this is the general name for a centre which acts as a source of light using the excitation light as input) are present at the interface between the sample and the prism, the volume that can contribute to the background radiation (this volume has order of magnitude of illuminated area times decay length of the evanescent field into the sample) due to e.g., luminophores not bound to the interface or the matrix/carrier (e.g., water) of the sample is significantly larger than the volume that contributes to luminescence of bound luminophores [signal]. As a consequence the signal to background (sometimes called noise) ratio is in most cases poor. An advantage of this arrangement is that a single illumination allows to measure/probe a large area of the interface between the prism and sample: short measurement times.

In order to increase the signal over background ratio a straightforward and well-known solution is to reduce the illumination area by e.g., using a focused spot. Disadvantage of this method is that probing a large area of the interface requires scanning of the single spot over the interface. Moreover, in case of luminescence it is useless to use higher excitation intensity than the saturation intensity, because this will not result in a higher fluorescent signal.

Patent application EP04106477.5 proposes the use of a multiple spot generator that generates an array of spots at the interface with the sample. Each individual spot can be seen as a collection of plane waves propagating towards the sample under different angles. Blocking the angles that are not total internally reflected at the interface with the sample (an would otherwise propagate into the sample, which is an undesired effect) by e.g., a mask with a period array of absorbing material results in an array of spots that are total internally reflected. Disadvantages of this method are:

The amount of excitation power that can be converted into the evanescent field is limited; portion of the spot propagating under angles not total internally reflected at the interface with the sample is blocked.

Scanning of the spots requires synchronization of the array of spots and the mask used for blocking.

Paths of the excitation light and luminescence light propagating in the backward direction overlap which requires a wavelength splitter/filter for separating the luminescence from the excitation light.

Similar arguments like those described above also hold for surface plasmon excitation with the main difference that efficient excitation of the surface plasmon wave requires a large part of the light to be in a small range of angles.

It is therefore an object of the present invention to provide a device, which allows a quicker detection without deterioration in resolution or accuracy and making use of the available excitation power in a more efficient way.

This object is solved by a device according to claim 1 of the present invention. Accordingly, a device for detecting excitation, in particular luminescent excitation in a fluid sample, comprising a transparent slab having a slab-sample interface a multiple spot generator provided with the slab, and a multiple spot arrangement provided on or in the vicinity of the slab-sample interface wherein the multiple spot generator is matched to the multiple spot arrangement in such a way that light entering the multiple spot generator will be guided to defined areas on the multiple spot arrangement.

By using such a device, one or more—depending on the actual application—of the following advantages can be reached:

The conversion of excitation power into evanescent waves is more efficient than in prior art solution; i.e., more power per spot compared with arrangement with mask with blocks and because that maximum useful power per spot is limited by saturation effects dividing the power over multiple spots results in more efficient use of the total power.

The optical paths of the excitation light (which is the light that enters the slab) and the luminescence (which is the light that is emitted by the sample) are better separated The device is usually simpler than those of the prior art The device does not require synchronisation of multiple spot arrangement with other optical elements (like a mask used for blocking).

The term "slab" in the sense of the present invention means especially a cuboid or prism-shaped device, which allows a multiple spot arrangement to be formed at an interface between the slab and the sample. According to a preferred embodiment, the slab is a prism; however, for other applications it may be preferred that the slab is cuboid-shaped.

The term "transparent" in the sense of the present invention means especially that the material is essentially transparent (sufficiently low losses) for light having the excitation wavelength and/or the luminescent wavelength.

The term "slab-sample interface" in the sense of the present invention means especially that at least one side of the slab is exposed to the excitation light or is directed towards the sample. This side is then called the interface. In case that surface plasmon resonance is used (as will be described below), there may be a surface plasmon layer provided between the slab and the sample. The "slab sample interface" is then provided with the side of the surface plasmon layer projecting towards the sample.

The term "multiple spot generator" in the sense of the present invention means especially a device that generates a spot pattern at the slab-sample interface having a well-defined amplitude and phase distribution. Preferably the multiple spot generator determines this way the intensity and angles of incidence with respect to the slab-sample interface.

The term "multiple spot arrangement" in the sense of the present invention means especially a spot pattern at the slab-sample interface having a well-defined amplitude and phase distribution.

The term "defined areas" in the sense of the present invention means especially certain areas on the slab-sample interface, towards which light from the multiple spot generator is directed to form the multiple spot arrangement.

According to a preferred embodiment of the present invention, the multiple spot generator comprises at least one diffractive element and/or a microlens arrangement. These have shown in practice to be suitable implementations for the multiple spot generator.

In case the multiple spot generator comprises a diffractive element it is preferred that the diffractive element employs one or more of the following features:

The diffractive element is equipped as to generate a multiple spot array at the interface between the slab and the sample.

The diffractive element should be transparent for excitation light.

In case the multiple spot generator comprises a microlens arrangement it is preferred that the microlens arrangement employs one or more of the following features:

In case the slab is a prism the microlenses have a varying focal length so that each individual micro-lens generates a spot that is focused on the interface between the slab and the sample.

In case the slab is cubic shaped the microlenses have a constant focal length and the lens array is illuminated with a tilted (with respect to the plane of the lens array) input beam, such that the spots at the interface have an angle of incidence larger than the total internal reflection angle.

According to a preferred embodiment of the present invention, the widths $w_{lens}(q)$ of the lenses in the microlens array are $$2w_f(q) \leq w_{lens}(q) \leq s$$

whereby the widths $w_{lens}(q)$ of the lenses are selected independently from each other and the $w_f(q)$ is the beam waist of each spot just behind the lens and s is the distance between the spots at the hypotenuse.

Preferably, the widths $w_{lens}(q)$ of the lenses in the microlens array are $$20.5 * w_f(q) \leq w_{lens}(q) \leq s * 0.8$$

whereby the widths $w_{lens}(q)$ of the lenses are selected independently from each other and the $w_f(q)$ is the beam waist of each spot just behind the lens and s is the distance between the spots at the hypotenuse.

Preferably $w_f(q)$ and the focal length $f_q$ of each lens (q) in the array are calculated by the following equations:

$$f_q = f_0 + qd\sin(\phi)$$

$$w_f(q) = \sqrt{w_0^2 + \frac{f_q^2 \lambda_p^2}{\pi w_0^2}}$$

with:

$f_0$, being the focal length of the microlens (lens 0) closest to the angle between the interface and the hypotenuse of the prism;

$\pi/2-\phi$ being the angle between the interface of the slab and the emitted light into the slab (I have taken this from FIG. 2), whereby the angle $\phi$ preferably is larger than the total internal reflection angle at the interface between slab and sample; and d being the pitch between the spots at the interface.

s and d are linked by the following equation.

$$s = d \cdot \cos(\phi)$$

According to a preferred embodiment of the present invention, the slab is a prism having a prism-sample interface with angles such that incident excitation light is totally internally reflected on a prism-sample interface. If we assume a plane wave incident normal to the tilted plane of the prism, preferably the angle of the prism $\phi$ is selected to be as follows:

$$\theta_{TIR} \leq \phi \leq \frac{\pi}{2}$$

with $\theta_{TIR}$ being the total internal reflection angle as the minimum angle with respect to the normal of the interface that results in total internal reflection:

$$\theta_{TIR} = \arcsin\left(\frac{n_{sample}}{n_{prism}}\right)$$

with $n_{sample}$ as the refractive index of the sample and $n_{prism}$ the refractive index of the prism.

If the angle is chosen between these margins, the incident light entering the prism will be totally internally reflected. For a(n) (array of) spot(s) the field can be expressed as a sum (integral) of plane waves. Each plane wave has a certain angle with respect to the interface between the slab/prism and the sample. Preferably, the angle of the prism $\phi$ is chosen somewhat larger than the lower boundary of the abovementioned relation for the prism angle.

According to a preferred embodiment of the present invention, the multiple spot generator is movable along or with the slab.

By doing so, one or more of the following advantages can be achieved:

The focus of the multiple spot arrangement can be kept better on the interface between the slab and the sample; in case of a slab that has at least one hypotenuse.

The alignment of the multiple spot generator with the slab can be improved.

In case of an interface between the multiple spot generator and the slab (essentially) parallel to the interface between the slab and the sample one can scan (in 2D) the array of focused spots in a plane (essentially) parallel to the interface between the slab and the sample.

According to a preferred embodiment of the present invention, the light that enters the diffractive element and/or the multiple spot generator is bent and/or guided in order to reach the multiple spot arrangement with an angle $\phi$ (with respect to the normal of the slab-sample interface) towards the slab-sample interface of $$\theta_{TIR} \leq \phi \leq \frac{\pi}{2}$$

with $\theta_{TIR}$ being the total internal reflection angle as the minimum angle with respect to the normal of the interface that results in total internal reflection:

$$\theta_{TIR} = \arcsin\left(\frac{n_{sample}}{n_{prism}}\right)$$

with $n_{sample}$ as the refractive index of the sample and $n_{prism}$ the refractive index of the prism.

According to a preferred embodiment of the present invention, the multiple spot generator is moved and/or translated along the hypotenuse of the prism. By doing so, a proper alignment of the spots generated by the multiple spot generator can be achieved in order to properly focus the array of spots on the interface between the prism and the sample.

According to a preferred embodiment of the present invention, the total internal reflection cone of the slab is set to fulfill the equation:

$$\theta_{TIR} \leq \phi \leq \frac{\pi}{2}$$

with $\theta_{TIR}$ being the total internal reflection angle as the minimum angle with respect to the normal of the interface that results in total internal reflection:

$$\theta_{TIR} = \arcsin\left(\frac{n_{sample}}{n_{prism}}\right)$$

with $n_{sample}$ as the refractive index of the sample and $n_{prism}$ the refractive index of the prism.

According to a preferred embodiment, the angle $\theta_m$, which is the maximum angle (relative to the normal of the interface between the slab and the environment) in the slab under which the generated luminescence can still be detected is set to fulfill the equation:

$$\theta_m \leq \arcsin\left(\frac{n_0}{n_p}\right)$$

with $n_o$ being the refractive index of the environment of the device (usually air) and $n_p$ the refractive index of the prism.

According to a preferred embodiment, with the multiple spot generator having a width W and the angles $\phi$ and $\theta_m$ being as described above, the thickness of the slab D is set to fulfill the equation:

$$D > D^*$$

with $D^*$ being $D^* = \frac{W}{\tan(\phi) - \tan(\theta_m)}$

Preferably, the thickness is set to be:
$1.5*D^* \leq D \leq 100*D^*$, more preferably $2*D^* \leq D \leq 10*D^*$ and most preferred $3*D^* \leq D \leq 8*D^*$ According to a preferred embodiment of the present invention, the intensity of the individual spots (generated by the multiple spot generator) at the interface between the slab and the sample is $\geq 1\ \mu W/(\mu m)^2$ and $\leq 1\ mW/(\mu m)^2$ According to a preferred embodiment of the present invention, the intensity of the individual spots (generated by the multiple spot generator) at the interface between the slab and the sample is (slightly) below the saturation intensity of the fluorophore/luminophore.

According to a preferred embodiment of the present invention, the multiple spot arrangement is a 1D or 2D arrangement.

According to a preferred embodiment of the present invention, the excitation is done via surface plasmon excitation. Instead of totally internally reflecting the multiple spots at the interface between a prism and a sample (resulting in evanescent fields in the sample), it is also possible to coat the slab interface facing towards the sample with a surface plasmon layer and excite short-range surface plasmon waves that propagate along the interface of the surface plasmon layer with the sample.

In the sense of the present invention a short range surface plasmon wave is especially a wave which propagates only a few microns along the interface between the surface plasmon layer and the sample. It is preferred that the propagation length should be at least smaller than the pitch between the spots of the multiple spot arrangement.

According to a preferred embodiment of the present invention, the surface plasmon layer is made out of a material selected out of the group comprising Au, Ag, Cr, Al or mixtures thereof. These materials have shown to be best suitable in practice.

According to a preferred embodiment of the present invention, the real index of the surface plasmon layer (normalized by index of sample) is $$0 \leq \text{real}\left(\frac{n_{SP}}{n_{sample}}\right) \leq 4$$

with a time dependence of $\exp(j*\omega*t)$ with $\omega$ the angular frequency of the light and t the time;

By doing so, a surface plasmon with practical values for the decay length of the evanescent tail into the sample can be achieved.

According to a preferred embodiment of the present invention, the real index of the surface plasmon layer (normalized by index of sample) is $$0.01 \leq \text{real}\left(\frac{n_{SP}}{n_{sample}}\right) \leq 1.5$$

with a time dependence of $\exp(j*\omega*t)$ with $\omega$ the angular frequency of the light and t the time.

According to a preferred embodiment of the present invention, the imaginary index of the surface plasmon layer (normalized by index of sample) is $$-7 \leq \text{imaginary}\left(\frac{n_{SP}}{n_{sample}}\right) \leq -0.2$$

with a time dependence of $\exp(j*\omega*t)$ with $\omega$ the angular frequency of the light and t the time.

According to a preferred embodiment of the present invention, the imaginary index of the surface plasmon layer (normalized by index of sample) is $$-3.3 \leq \text{imaginary}\left(\frac{n_{SP}}{n_{sample}}\right) \leq -0.6$$

with a time dependence of exp(j*ω*t) with ω the angular frequency of the light and t the time.

This has also shown in practice to achieve a surface plasmon with practical values for the decay length of the evanescent tail into the sample.

According to a preferred embodiment of the present invention, the thickness of the surface plasmon layer is $\geq 10$ nm and $\leq 350$ nm, preferably $\geq 70$ nm and $\leq 300$ nm. These margins have proven themselves to be best suitable in practice.

According to a preferred embodiment of the present invention, the surface plasmon layer is made out of an gold material and the real index of the surface plasmon layer (normalized by index of sample) is $$0 \leq \text{real}\left(\frac{n_{SP}}{n_{sample}}\right) \leq 3.1$$

with a time dependence of exp(j*ω*t) with ω the angular frequency of the light and t the time.

According to a preferred embodiment of the present invention, the surface plasmon layer is made out of an silver material and the real index of the surface plasmon layer (normalized by index of sample) is $$0 \leq \text{real}\left(\frac{n_{SP}}{n_{sample}}\right) \leq 0.8$$

with a time dependence of exp(j*ω*t) with ω the angular frequency of the light and t the time.

According to a preferred embodiment of the present invention, the surface plasmon layer is made out of an chromium material and the real index of the surface plasmon layer (normalized by index of sample) is $$2.0 \leq \text{real}\left(\frac{n_{SP}}{n_{sample}}\right) \leq 3.8$$

with a time dependence of exp(j*ω*t) with ω the angular frequency of the light and t the time.

According to a preferred embodiment of the present invention, the surface plasmon layer is made out of an Aluminum material and the real index of the surface plasmon layer (normalized by index of sample) is $$0.8 \leq \text{real}\left(\frac{n_{SP}}{n_{sample}}\right) \leq 2.1$$

with a time dependence of exp(j*ω*t) with ω the angular frequency of the light and t the time.

According to a preferred embodiment of the present invention, the surface plasmon layer is made out of an gold material and the imaginary index of the surface plasmon layer (normalized by index of sample) is $$-3.3 \leq \text{imaginary}\left(\frac{n_{SP}}{n_{sample}}\right) \leq -0.6$$

with a time dependence of exp(j*ω*t) with ω the angular frequency of the light and t the time.

According to a preferred embodiment of the present invention, the surface plasmon layer is made out of an Silver material and the imaginary index of the surface plasmon layer (normalized by index of sample) is $$-4.5 \leq \text{imaginary}\left(\frac{n_{SP}}{n_{sample}}\right) \leq -2.8$$

with a time dependence of exp(j*ω*t) with ω the angular frequency of the light and t the time.

According to a preferred embodiment of the present invention, the surface plasmon layer is made out of an Chromium material and the imaginary index of the surface plasmon layer (normalized by index of sample) is $$-4.5 \leq \text{imaginary}\left(\frac{n_{SP}}{n_{sample}}\right) \leq -1.9$$

with a time dependence of exp(j*ω*t) with ω the angular frequency of the light and t the time.

According to a preferred embodiment of the present invention, the surface plasmon layer is made out of an Aluminum material and the imaginary index of the surface plasmon layer (normalized by index of sample) is $$-7 \leq \text{imaginary}\left(\frac{n_{SP}}{n_{sample}}\right) \leq -5.3$$

with a time dependence of exp(j*ω*t) with ω the angular frequency of the light and t the time.

According to an embodiment of the present invention, the multiple wavelength generator comprises at least one polarization device so that at least one of the spots of the at least one array of spots comprises polarized light. This has for most applications the advantage that reflected light may be blocked by a blocking means as will be described later on.

According to an embodiment of the present invention, the multiple wavelength generator comprises at least one polarization filter that transmits one polarization state (ps1) and does not transmit or reflect another (orthogonal) polarization state (ps2);

According to an embodiment of the present invention, the multiple wavelength generator comprises at least one polarization rotator which rotates the polarization state by a rotation angle of δφ1 degrees.

According to a preferred embodiment of the present invention, the multiple wavelength generator comprises a blocking means which blocks the light or parts thereof generated by the multiple wavelength generator.

According to a preferred embodiment of the present invention, the multiple wavelength generator comprises a first blocking means which blocks one polarization component (polarization state 2; ps2) of the light generated by the multiple wavelength generator and transmits the other polarization component (polarization state 1; ps1) and a second blocking means which blocks the light reflected by at the slab-sample interface.

According to an embodiment of the present invention, the blocking means comprises a polarization filter and/or a polarization rotator.

According to an embodiment of the present invention, the blocking means comprises at least one polarization rotator that rotates the polarization state by δφ2 degrees such that |δφ1+δφ2|=90 degrees.

According to an embodiment of the present invention, the polarization device polarizes the device to p/s polarized light and the blocking means blocks p/s polarized light and/or the polarization device polarizes the device to s/p polarized light and the blocking means blocks s/p polarized light.

According to an embodiment of the present invention, the device comprises a first blocking means which comprises a polarization filter that blocks polarization state ps2 and/or a polarization rotator that rotates the polarization angle by δφ1 degrees and a second blocking means which comprises a polarization filter and/or a polarization rotator that rotates the polarization angle by δφ2 degrees. According to an embodiment of the present invention, the polarization rotators are configured such that |δφ1+δφ2|=90 degrees.

A device according to the present invention may be of use in a broad variety of systems and/or applications, amongst them one or more of the following:

biosensors used for molecular diagnostics rapid and sensitive detection of proteins and nucleic acids in complex biological mixtures such as e.g. blood or saliva high throughput screening devices for chemistry, pharmaceuticals or molecular biology testing devices e.g. for DNA or proteins e.g. in criminology, for on-site testing (in a hospital), for diagnostics in centralized laboratories or in scientific research tools for DNA or protein diagnostics for cardiology, infectious disease and oncology, food, and environmental diagnostics tools for combinatorial chemistry analysis devices The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, features, characteristics and advantages of the object of the invention are disclosed in the subclaims, the figures and the following description of the respective figures and examples, which—in an exemplary fashion—show several preferred embodiments of a device according to the invention.

Figure 1:
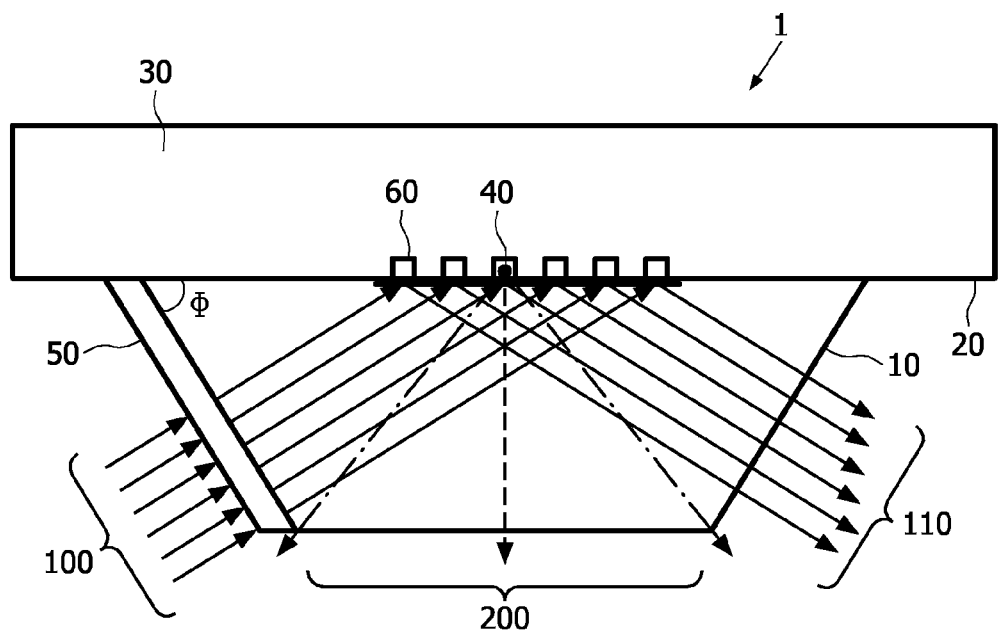
FIG. 1 shows a very schematic cross-sectional view of a device according to a first embodiment of the present invention.

FIG. 1 shows a very schematic cross-sectional view of a device 1 according to a first embodiment of the present invention The device comprises a slab 10 in form of a prism, which has an interface 20 with the sample 30. The sample 30 is an aqueous or fluidic medium, in which luminescent, preferably fluorescent-marked biomolecules 40 are present.

The device furthermore comprises a multiple spot generator in form of a diffraction element 50. This diffraction element corresponds with a multiple spot arrangement (as indicated by 60) on the interface 20 of the prism 10. Incident light 100, which enters the prism via the diffraction element is guided and transformed into multiple spots at the interface 20 to the multiple spot arrangement 60; the light total internally reflected so the multiple spot arrangement penetrates into the sample as evanescent light) is then reflected (as indicated by numeral 110). However, in case that a biomolecule is present in the evanescent part of the multiple spot arrangement, fluorescent light (as indicated by the dotted lines 200) is emitted and may be detected, thus indicating the presence of the biomolecule 40 in the sample 30.

In order to distinguish the fluorescent light 200 from the incident light 100 and the reflected light 110, the angle φ of the prism 10 and the total cone of reflection are chosen to be as described above

EXAMPLE 1

The spot arrangement of the first embodiment of the present invention as shown in FIG. 1 and as described above will further be illustrated—in a mere exemplarily way—by the following example 1.

In this example, a 2D array of spots is generated by the multiple spot generator (in this embodiment a diffractive element). The excitation intensity is set to be slightly lower than the saturation intensity.

The 2D array is set to be circular spots with a diameter of 0.5 microns (area per spot of 0.2 μm2) for typical saturation intensities of a 1 μW/(μm)2 up to 1 mW/(μm)2, thus resulting in a power per spot of 5 μW to 5 mW per spot. For a laser/LED/other type of light source with a total power of 10-100 mW this results in a possible number of spots between 2-20000 spots. Assuming an illuminated area of 1 mm2 (at the interface between slab and sample), the area to be scanned by each spot is 50 (μm)2 up to 0.5 mm2 corresponding with a pitch between the spots of 7 μm up to 0.7 mm.

It should be noted that it is clear for any person skilled in the art that such a spot arrangement may also be of use for any other embodiment, either those that are described below or that are also apparent to be within the present invention.

Figure 2:
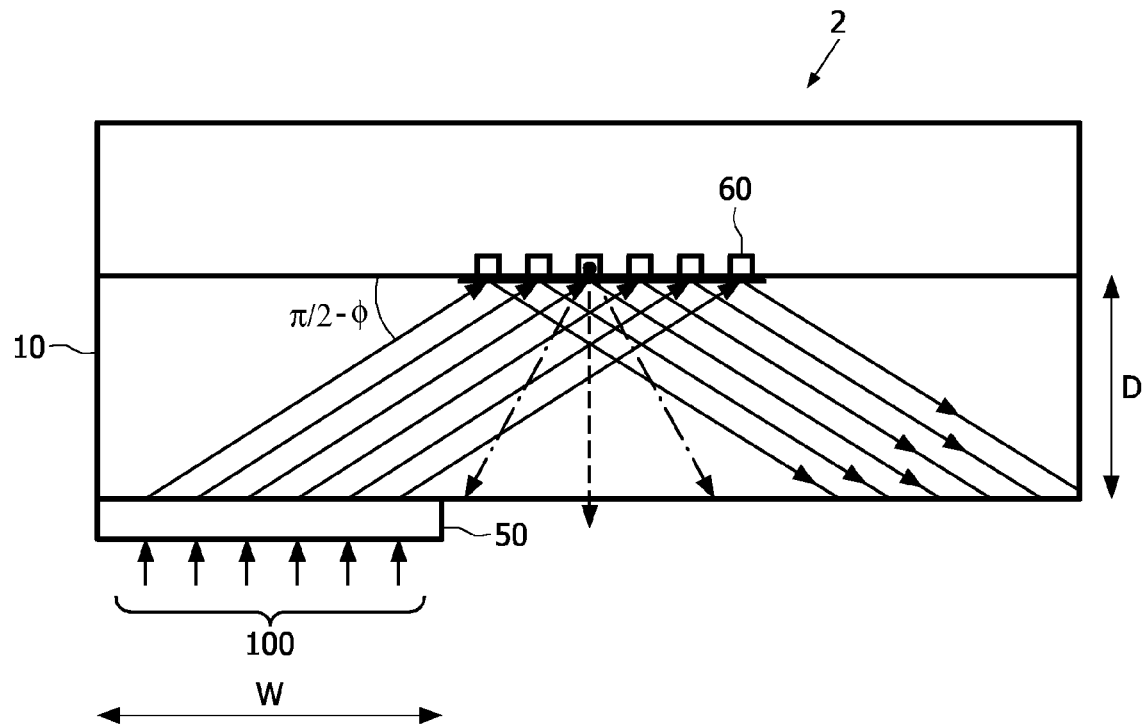
FIG. 2 shows a very schematic cross-sectional view of a device according to a second embodiment of the present invention.

FIG. 2 shows a very schematic cross-sectional view of a device 2 according to a second embodiment of the present invention. This device 2 differs from the embodiment as shown in FIG. 1 in that that the slab 10 is rectangular when seen in the cross-sectional view (as shown in FIG. 2) and that a movable diffractive element 50 is used. This diffractive element has a width W. Incident light 100, which enters the prism via the diffraction element 50 is guided to the multiple spot arrangement 60 and is bent by the diffraction element 50 in an angle φ which is set to be in the range of:

$$\theta_{TIR} \le \phi \le \frac{\pi}{2}$$

The thickness D of the slab 10 is preferably 1.5*D* ≤ D ≤ 10*D* with D* being as described above.

In this embodiment, it is preferred that the diffractive element 50 is designed such that the multiple spot arrangement 60 (and therefore also the structure of the diffractive element 50) is periodic (i.e., each spot has the same distance along the direction of propagation to the interface with the sample). This allows that the scanning of the spots is straightforward and can be performed by translating the diffractive element 50 along the surface of the slab 10.

EXAMPLE 2

The second embodiment of the present invention as shown in FIG. 2 and as described above will further be illustrated—in a mere exemplarily way—by the following example 2.

In this example, the following features were set for the device:

Slab: index of refraction $n_p=1.68$

Sample: measurand (e.g. the molecules to be detected) are in a water environment (i.e., water is the sample) having an index $n_s=1.3$.

Environment: the system is in an air environment having an index of refraction $n_0=1$.

Multiple spot generator: Width W=1 mm, angle $\phi=60$ degrees

For the chosen refractive indexes avoiding total internal reflection at the interface between the slab and the environment requires angles $\theta_m<36.5$ degrees being smaller than the minimum value for $\phi$ for total internal reflection at the slab-sample interface, which is set to be $\phi>50.7$ degrees. Taking in account the features of the multiple spot generator and assuming that $\theta_m$ is limited by total internal reflection we find a minimum thickness of the slab D>2.08 mm.

Figure 3:
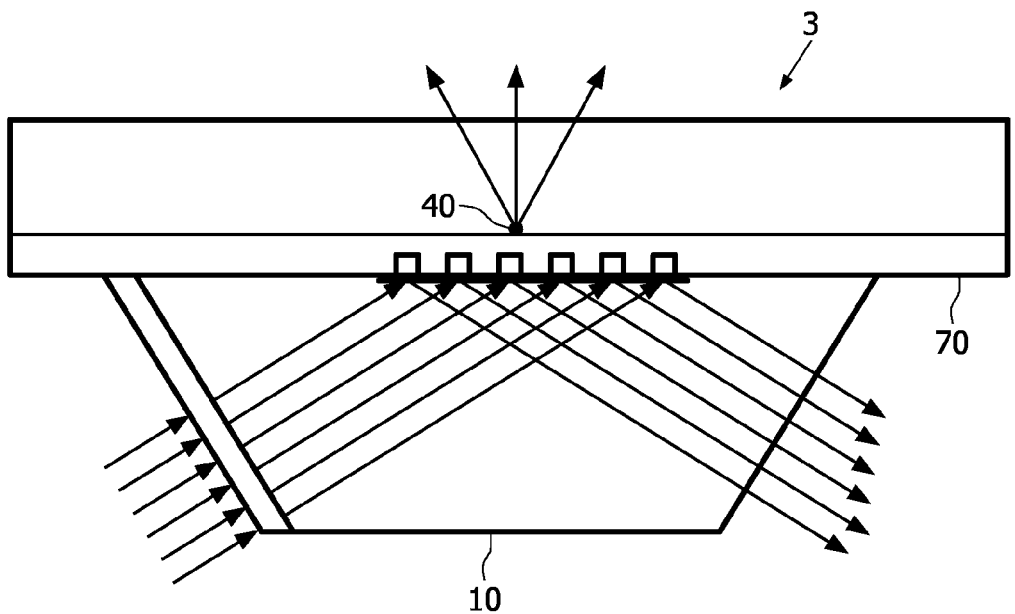
FIG. 3 shows a very schematic cross-sectional view of a device according to a third embodiment of the present invention.

FIG. 3 shows a very schematic cross-sectional view of a device 3 according to a third embodiment of the present invention. In this embodiment 3, surface plasmon resonance is used to cause emittance of the marked biomolecule 40. For these reasons, the slab 10 is covered with a surface plasmon layer 70. This so called surface plasmon layer has a refractive index $n_{SP}$ and is preferably made out of a material as described above.

EXAMPLE 3

The second embodiment of the present invention as shown in FIG. 3 and as described above will further be illustrated—in a mere exemplarily way—by the following example 3.

In this example, the following features were set for the device:

prism: index of refraction $n_p=1.68$ layer: gold layer with a index of refraction: $n_m=0.16-j*3.8$, for a wavelength of 688.8 nm medium water $n_s=1.3$ In this case, the surface plasmon wave has an effective index $n_{eff}=1.383-j*0.0077$; $(1/e)^2$ decay length of 232 nm in the sample and 27 nm in the gold layer; and a decay length in the direction of propagation of 14 μm.

Figure 5:
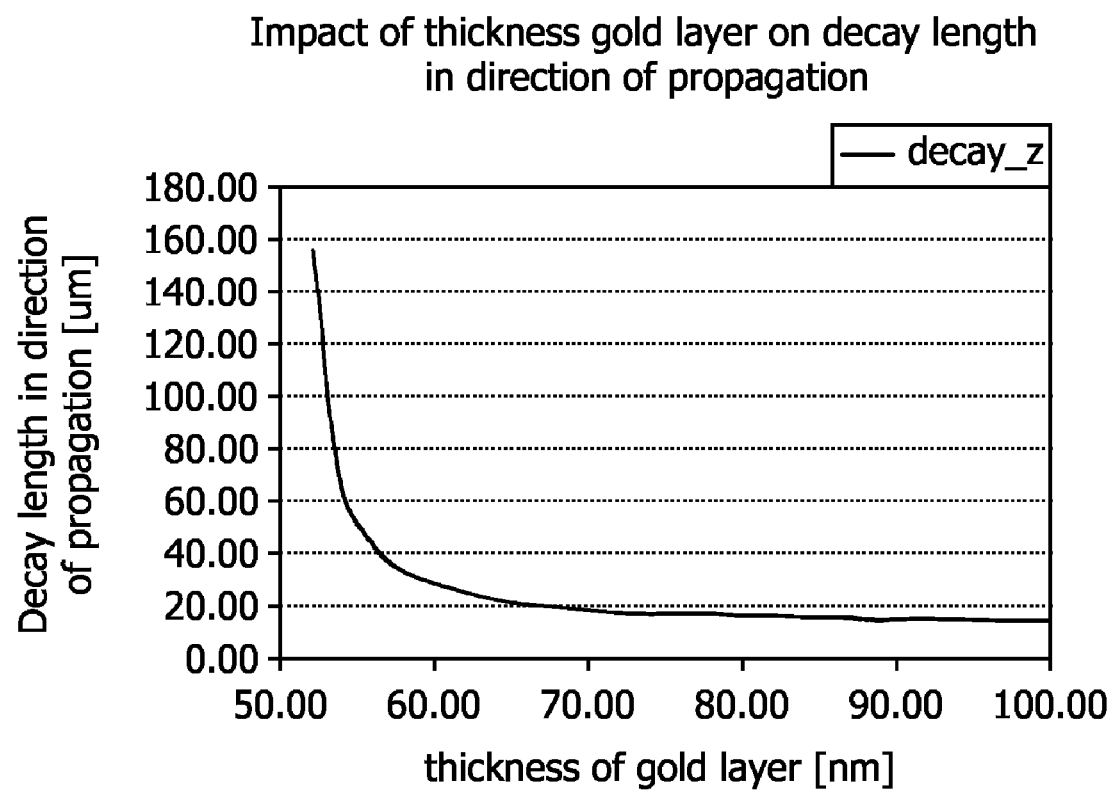
FIG. 5 is a diagram showing the impact of the thickness of the gold layer on the decay lengths in the direction of propagation.

The impact of the thickness of the gold layer on the decay lengths in the direction of propagation is shown in FIG. 5. It can be seen from the picture, that the decay length into the direction of propagation decreases towards the decay length for a semi-infinite gold layer for increasing thickness of the surface plasmon layer.

In the example, a gold layer of 70 nm thickness was chosen, resulting in the following:

Decay length smaller than 20 microns.

Reasonably efficient excitation: intensity reflection of 35.6%, which corresponds with about 50% of the input power converted into the surface plasmon wave.

Figure 4:
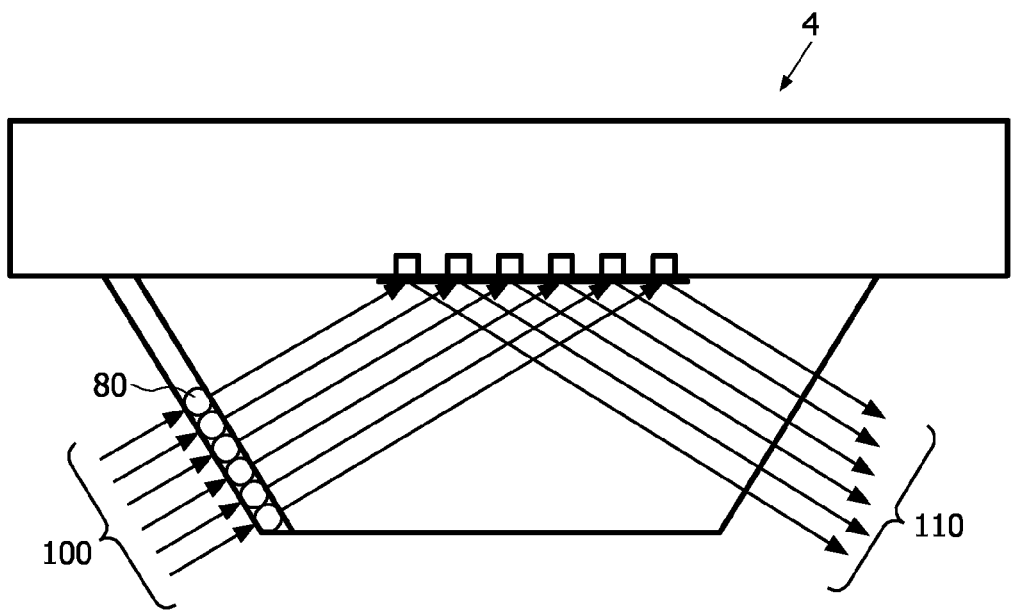
FIG. 4 shows a very schematic cross-sectional view of a device according to a fourth embodiment of the present invention.

FIG. 4 shows a very schematic cross-sectional view of a device 4 according to a fourth embodiment of the present invention. This embodiment is similar to that of FIG. 1 except that microlenses 80 were used instead of a diffractive element. For reasons of clarity, only the way of the incident light 100 and the reflected light 110 is shown, although this embodiment works in the same way as that shown in FIG. 1.

It should be noted, that microlenses 80 instead of a diffractive element 50 may be used within the embodiments as shown in FIGS. 2 and 3, too.

EXAMPLE 4

The fourth embodiment of the present invention as shown in FIG. 4 and as described above will further be illustrated—in a mere exemplarily way—by the following example 4.

For a prism with index of refraction np=1.68 and an excitation wavelength of 600 nm we find λ=357.14 nm, which is the wavelength in the medium of the prism. Taking a prism angle of 60 degrees, a pitch between spots of 100 microns and a focal length of 1 mm, we find:

a pitch between lenses of lens array of s=50 microns.

a minimum beam waist of 4.5 microns of the Gaussian beam a minimum beam waist of 9.0 microns of the projection of the Gaussian beam on the interface between the slab/prism and the sample.

Another embodiment furthermore comprises two polarizing means, of which one of the polarizing means also serves as blocking means.

In the present embodiment, the light, after passing through the diffraction element, passes a polarizing means in form of a polarization filter that transmits one polarization state (ps1) and does not transmit or reflect the other (orthogonal) polarization state (ps2); light having polarization state ps2 is absorbed by the polarization filter. Subsequently, the light enters a polarization rotator which rotates the polarization state by a rotation angle of $\delta\phi 1$ degrees.

In case that a biomolecule is present in the evanescent part of the multiple spot arrangement, fluorescent light is emitted and may be detected, thus indicating the presence of the biomolecule in the sample.

However, most of the light will be reflected towards the second blocking means. This second blocking means also comprises a polarization rotator that rotates the polarization state by $\delta\phi 2$ degrees such that $|\delta\phi 1+\delta\phi 2|=90$ degrees. However, due to the presence of a polarization filter in the blocking means, too, this light will then be blocked and not leave the blocking means. As a result, the light that is reflected within the prism is blocked from leaving the device.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. A device for detecting luminescent excitation in a fluid sample, the device comprising:
    a transparent slab having a slab-sample interface with the fluid sample; and
    a multiple spot generator in contact with the slab, the multiple spot generator being configured to generate a multiple spot arrangement on or in the vicinity of the slab-sample interface, wherein the multiple spot generator is configured to move along a surface of the slab and to guide incident light entering the multiple spot generator through the slab to a corresponding spot of the multiple spot arrangement, the guided incident light penetrating the fluid sample, which emits luminescent light when a biomolecule is present in the fluid sample.

2. The device according to claim 1, wherein the slab comprises a prism and the slab-sample interface comprises a prism-sample interface having angles such that the incident light is totally internally reflected on the prism-sample interface and wherein an angle of the prism $\phi$ is selected to be as follows:

$$\theta_{TIR} \leq \phi \leq \frac{\pi}{2}$$

with $\theta_{TIR}$ being a total internal reflection angle as a minimum angle with respect to a normal of the prism-sample interface that results in total internal reflection:

$$\theta_{TIR} = \arcsin\left(\frac{n_{sample}}{n_{prism}}\right).$$

3. The device according to claim 1, wherein a total internal reflection cone $\phi$ of the slab is $$\theta_{TIR} \leq \phi \leq \frac{\pi}{2}$$

with $\theta_{TIR}$ being a total internal reflection angle as a minimum angle with respect to a normal of the prism-sample interface that results in total internal reflection.

4. The device according to claim 1, wherein intensity of spots of the multiple spot arrangement is $\geq 1$ µW/(µm)$^2$ and $\leq 1$ mW/(µm)$^2$.

5. The device according to claim 1, wherein the slab comprises a prism having thickness D, where $$D > D^*$$
$$\text{with } D^* \text{ being } D^* = \frac{W}{\tan(\phi) - \tan(\theta_m)}$$

wherein W is a width of the multiple spot generator, $\phi$ is an angle of the prism relative to the interface, and $\theta_m$ is a maximum angle in the slab, relative to a normal of the interface between the slab and the sample, under which the luminescence light can still be detected.

6. The device according to claim 1, wherein wherein the multiple spot generator comprises microlenses and further widths $w_{lens}(q)$ of microlenses in the microlens arrangement are $$2w_i(q) \leq w_{lens}(q) \leq s$$

wherein the widths $w_{lens}(q)$ are selected independently from each other and the $w_i(q)$ is a beam waist of each spot just behind the corresponding microlens and s is distance between the spot and an hypotenuse.

7. The device according to claim 1, wherein the detection is done via surface plasmon excitation of a surface plasmon layer.

8. The device according to claim 7, wherein a real index of the surface plasmon layer, normalized by index of the sample, is $$0 \leq \text{real}\left(\frac{n_{SP}}{n_{sample}}\right) \leq 4$$

and an imaginary index of the surface plasmon layer, normalized by index of the sample, is $$-7 \leq \text{imaginary}\left(\frac{n_{SP}}{n_{sample}}\right) \leq -0.2$$

with a time dependence of exp(j*ω*t) with ω being angular frequency of the incident light and t being time.

9. The device according to claim 1, wherein the slab comprises a prism, and the multiple spot generator comprises a plurality of microlenses having varying focal lengths so that each microlens generates the corresponding spot of the multiple spot arrangement that is focused on the interface between the slab and the sample.

10. The device according to claim 1, wherein the slab comprises a cubic shape, and the multiple spot generator comprises a plurality of microlenses having a constant focal length, the multiple spot generator being illuminated with a tilted input beam of the incident light.

11. A device for detecting luminescent excitation in a fluid sample, the device comprising:
a transparent slab comprising first and second surfaces, the slab having a slab-sample interface with the fluid sample at the first surface; and
a multiple spot generator comprising a microlens array in contact with the slab and movable along the slab at the second surface, the microlens array comprising a plurality of microlenses configured to respectively focus incident light entering the multiple spot generator and passing through the transparent slab onto corresponding defined areas at or near the slab-sample interface at the first surface, the incident light penetrating the fluid sample at the defined areas.

12. The device according to claim 11, wherein the slab comprises a prism, such that the second surface intersects the first surface at a predefined angle, and the microlenses have varying focal lengths so that each microlens generates a spot at a corresponding defined area at or near the slab-sample interface.

13. The device according to claim 11, wherein the slab comprises a cubic shape, such that the second surface is substantially parallel to the first surface, and the microlenses have a constant focal length.

14. The device according to claim 13, wherein the incident light enters the multiple spot generator at an angle with respect to a plane of the microlens array.

15. The device according to claim 14, wherein spots at the slab-sample interface have an angle of incidence larger than a total internal reflection angle of the slab.

16. A device for detecting luminescent excitation in a fluid sample, the device comprising:
a transparent slab comprising a first surface and a second surface substantially parallel to the first surface, the first surface of the slab comprising a slab-sample interface with the fluid sample; and
a microlens array contacting the second surface of the slab, the microlens array comprising a plurality of microlenses configured to respectively focus incident light through the slab to generate a spot pattern at or near the slab-sample interface at the first surface of the slab, the incident light penetrating the fluid sample at the spot pattern as evanescent light, wherein the microlens array is movable along the second surface of the slab, enabling scanning of the defined areas of the multiple spot arrangement.

* * * * *